(12) United States Patent
Hsieh et al.

(10) Patent No.: US 8,138,166 B2
(45) Date of Patent: Mar. 20, 2012

(54) METHOD TO INDUCE FATTY LIVER IN ANIMAL

(75) Inventors: Rong-Hong Hsieh, Taipei (TW); Sheng-Mei Lin, Taichung County (TW)

(73) Assignee: Taipei Medical University, Taipei (TW)

( * ) Notice: Subject to any disclaimer, the term of this patent is extended or adjusted under 35 U.S.C. 154(b) by 123 days.

(21) Appl. No.: 12/803,850

(22) Filed: Jul. 8, 2010

(65) Prior Publication Data
US 2011/0178045 A1   Jul. 21, 2011

(30) Foreign Application Priority Data
Jan. 19, 2010   (TW) ................ 99101414 A

(51) Int. Cl.
*A61K 31/655* (2006.01)
*A61K 31/515* (2006.01)
*A61K 31/44* (2006.01)
*A61K 31/335* (2006.01)
*A61K 31/35* (2006.01)
*A61K 31/275* (2006.01)

(52) U.S. Cl. ........ 514/150; 514/270; 514/348; 514/450; 514/453; 514/519; 514/706

(58) Field of Classification Search ............. 514/150, 514/270, 348, 450, 453, 519, 706
See application file for complete search history.

(56) References Cited

U.S. PATENT DOCUMENTS 7,469,185 B2 * 12/2008  Mendrick et al. ............. 702/19
2007/0015147 A1 *  1/2007  Mendrick et al. ............. 435/6

* cited by examiner

*Primary Examiner* — Raymond Henley, III
(74) *Attorney, Agent, or Firm* — Hudak, Shunk & Farine Co. LPA

(57) ABSTRACT

The present invention discloses a method to induce fatty liver in an animal. The steps of the method comprise: feeding an animal with a high calorie diet, and injecting a mitochondrial inhibitor into the animal to inhibit the mitochondrial activity of the animal, then resulting in fat accumulation and inflammation in the liver of the animal.

15 Claims, 2 Drawing Sheets

(A)

(B)

(C)

METHOD TO INDUCE FATTY LIVER IN ANIMAL

FIELD OF THE INVENTION

The present invention relates to a method; and more particularly, to a method to induce fatty liver in an animal.

BACKGROUND OF THE INVENTION

Recently, a nonalcoholic fatty liver disease (NAFLD) is a growing medical problem in many countries, and may progress to an end stage liver disease. The feature of causing the NAFLD is without excess alcohol consumption, that is, the amount of alcohol intake is less than 20~40 g ethanol for men and less than 20 g ethanol for women. The NAFLD refers to a wide spectrum of liver diseases comprising simple steatosis, nonalcoholic steatohepatitis (NASH) developed from steatosis, even cirrhosis, liver failure or a liver tumor developed from NASH.

Mitochondrion is a double membrane organelle existing in the cytoplasm of eukaryotic cells. According to different types of cells, hundreds to thousands of mitochondria are found. The mitochondrion is composed of compartments responsible for various specialized functions. These compartments include an inner membrane, an outer membrane, an intermembrane space, and a matrix. There are many inward folds called as cristae formed on the inner membrane. The cristae are studded with many proteins to use for aerobic respiration and to produce adenosine triphosphates (ATPs). The proteins producing ATPs are electron transport chain (ETC) enzymes including mitochondrial complex I to V (NADH dehydrogenase, succinate dehydrogenase, ubiquinol-cytochrome c oxidoreductase, cytochrome c oxidase, ATP synthase) for providing energy to cells.

Increasing oxidative stress in cells is an important pathophysiological mechanism of the NASH. In previous studies, free radicals are generated certainly from mitochondria in liver of a mammal. At normal physiological conditions, only 0.15% electrons are combined with oxygen to form superoxide anion radicals ($O_2.^-$). The $O_2.^-$ is converted into hydrogen peroxide ($H_2O_2$) by manganese-superoxide dismutase (Mn-SOD), and then the $H_2O_2$ is converted into $H_2O$ and $O_2$ by various anti-oxidative enzymes in cells. Once mitochondrial dysfunction is occurred, the $O_2.^-$ production may be significantly increased to result in lipid peroxidation from polyunsaturated fatty acids, such that the formation of lipid peroxides, such as thiobarbituric acid-reactive-substance (TBARS), is increased. The half life of the lipid peroxides is longer than the half life of reactive oxygen species (ROS), and the lipid peroxides may be spread to the vicinity of the cells, thus amplifying the effects of the oxidative stress. However, in the process of transferring elections, $O_2.^-$ is majorly formed via leaking an electron from mitochondrial complex I and III and coupling with oxygen.

Recently, the number of patients accepting the NAFLD treatment is small, and the tracking duration thereof is not very long. In previous studies, laboratory animals are fed with high calorie diets to induce the NAFLD, thereby imitating fat accumulation in a liver of a human. Simple steatosis is reversible, i.e. when the laboratory animals are without feeding a high calorie diet, the amount of fat in the liver thereof are decreased. Therefore, it is a difficulty to achieve liver inflammation.

SUMMARY OF THE INVENTION

In view of the aforementioned drawbacks in the prior art, an object of the present invention is to provide a method to induce fatty liver in an animal, so as to establish an animal model for fat accumulation and inflammation in a liver thereof.

To achieve the above object, the method to induce fatty liver in the animal comprises the following steps. An animal is fed with a high calorie diet. A mitochondrial inhibitor is injected into the animal to inhibit mitochondrial activity and to cause fat accumulation and inflammation in the liver of the animal.

Accordingly, the method to induce fatty liver in the animal according to the present invention may provide one or more of the following advantages:

(1) According to the method of the present invention, the mitochondrial activity is decreased via injecting a mitochondrial inhibitor to cause mitochondrial dysfunction and increase oxidative stress, resulting in inflammation reaction in vivo, and thereby establishing an animal model of the nonalcoholic steatohepatitis (NASH).

(2) According to the method of the present invention, the progression of simple steatosis to the NASH is achieved rapidly. Via injecting the mitochondrial inhibitor, it indicates that mitochondrial dysfunction is a reason of causing the NASH.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

The present invention will now be described with some preferred embodiments thereof with reference to the accompanying drawings. It is understood the experimental data shown in the embodiments are provided only for easy interpretation of the technical means of the present invention and should in no means be considered as restriction to the present invention.

Embodiment 1

A Method to Induce Fatty Liver in an Animal

Figure 1:
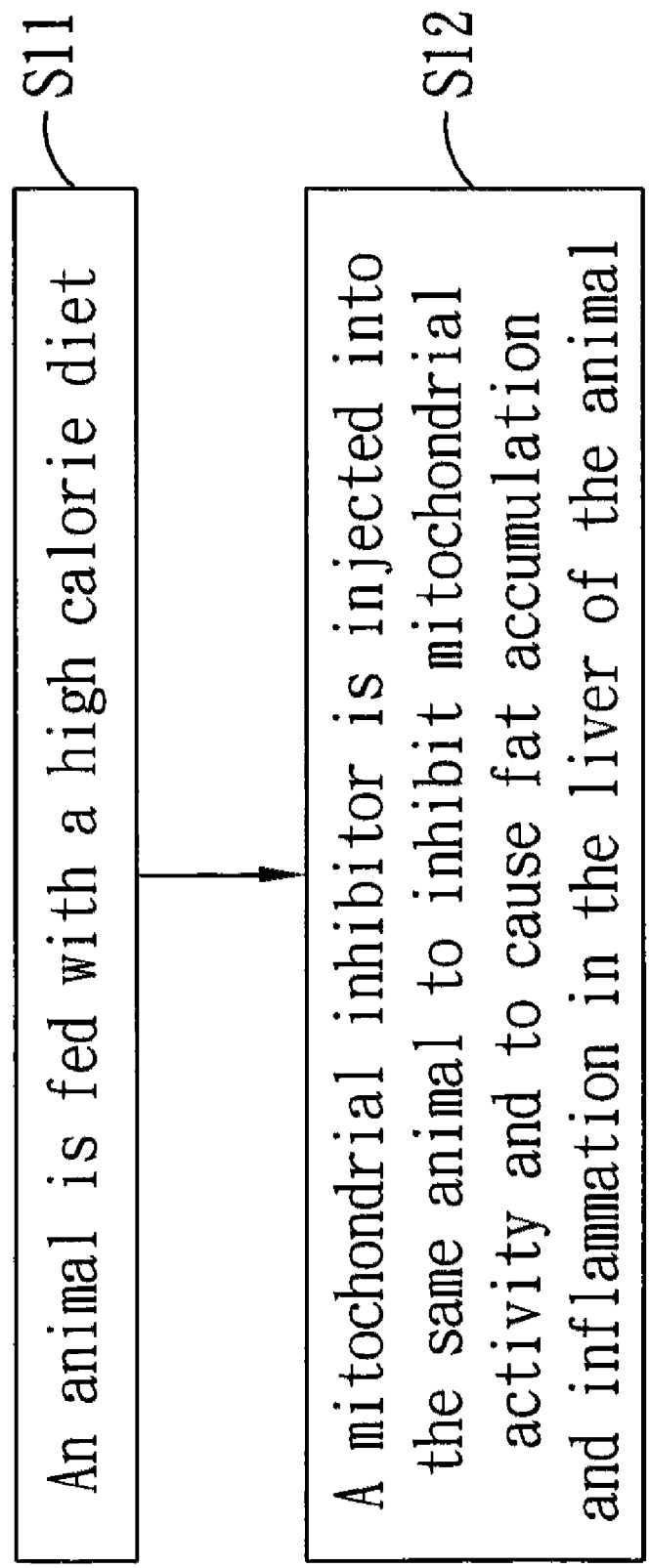
FIG. 1 is a flowchart showing a method to induce fatty liver in an animal according to the present invention.

Please refer to FIG. 1 that is a flowchart showing a method to induce fatty liver in an animal according to the present invention, comprising steps as follows. In step S11, an animal is fed with a high calorie diet. In step S12, a mitochondrial inhibitor is injected into the same animal to inhibit mitochondrial activity and to cause fat accumulation and inflammation in the liver of the animal. The mitochondrial inhibitor is injected into the animal by an intraperitoneal injection, an intramuscular injection, or an intravenous injection. The animal may be a rodent, such as a rat or a mouse. Wherein, a species of the rat comprises Spraque-Daley, Spontaneously Hypertensive (SHR), Wistar, or Lewts, and a species of the mouse comprises ICR, Balb/c, or C57BL6. Said high calorie diet may comprise a high fat diet, a high carbohydrate diet, a high fat and a high carbohydrate diet, or a high cholesterol diet. Fat calories of the high fat diet, carbohydrate calories of the high carbohydrate diet, or fat and carbohydrate calories of the high fat and high carbohydrate diet are in a range from 35% to 80% total calories. Additionally, cholesterol in the high cholesterol diet is extra added therein, and the amount of the cholesterol is in a range from 0.1 to 2 wt % of the diet.

Types of the mitochondrial inhibitor comprises a mitochondrial complex I inhibitor, a mitochondrial complex III inhibitor, a mitochondrial complex IV inhibitor, or an adenosine triphosphate (ATP) synthase inhibitor. The mitochondrial complex I inhibitor may comprise amytal, barbiturate, piericidin, or rotenone, and the mitochondrial complex III inhibitor may comprise antimycin A or dimercaprol. Further, the mitochondrial complex IV inhibitor may comprise cyanide, sulfide or azide, and the ATP synthase inhibitor may comprise oligomycin. A dosage of the rotenone injected into the animal is in a range from 0.1 to 4.0 mg/kg every time. If dosages are overloaded, the animals may be died. Preferably, dosages of the antimycin A, the dimercaprol, the cyanide, the sulfide, the azide and oligomycin may be in a range from 15 to 25 mg/kg, 80 to 120 mg/kg, 0.1 to 5 mg/kg, 5 to 20 mg/kg and 0.1 to 2 mg/kg, respectively.

Embodiment 2

Preferred Embodiments of the Present Invention

Experimental Design

SD rats are selected to use as the laboratory animals in the present embodiment. All SD rats are bred at the cages, and adequate feeds and water are given during the adaptive period and the experimental period. After the adaptive period, the SD rats are randomly divided into three groups concluding a control group, an experimental group, and a contrast group, and there are 6 SD rats in each group. In the control group, the SD rats are fed with AIN-93M diet. The SD rats in the experimental group are fed with the modified AIN-93M diet whose fat calorie is accounted for 60% of total calorie thereof, and the mitochondrial inhibitor (rotenone) is injected into the SD rats via an intraperitoneal injection once every two days. The dosage of the rotenone is about 2.5 mg/kg/day. The components of the diet and the fat percentage in the contrast group and the experimental group are the same. Normal saline is injected into the SD rats in the contrast group via the intraperitoneal injection to differentiate from the experimental group. After feeding 8 weeks, the SD rats in each group are sacrificed to collect arteria coeliaca blood and to obtain livers after perfusing 0.9% normal saline thereinto for determining the pathological analysis of the liver, the blood biochemical analysis and the liver biochemical analysis.

Liver Histopathology

Figure 2:
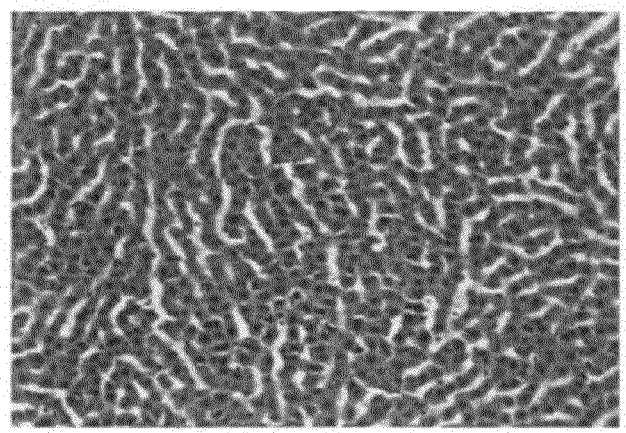
FIG. 2, views (A), (B) and (C) staining of liver biopsy of rats according to an embodiment of the present invention.
Figure 2:
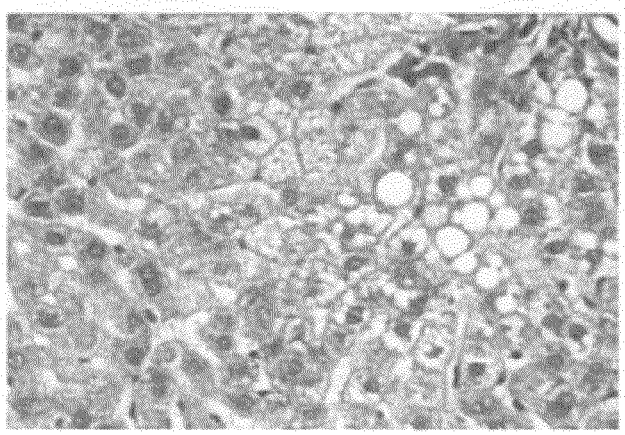
Figure 2:
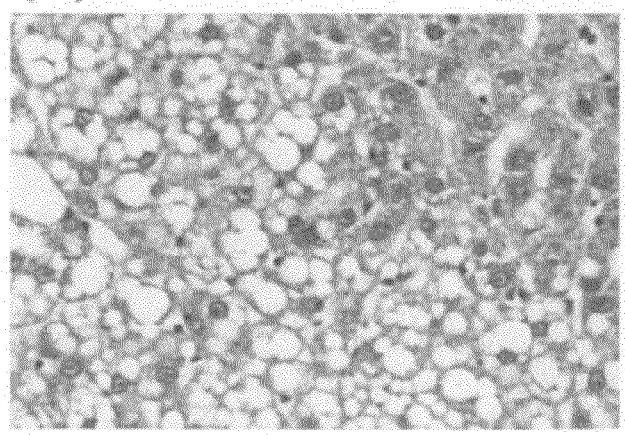

Livers of the SD rats in each group are all stained by H&E staining. Compared with the cell morphology in the control group, the cell morphologies in the experimental group and the contrast group have obviously changes, comprising generating lipid drops and ballooning degeneration. The ballooning degeneration is the feature of the nonalcoholic steatohepatitis. H&E staining of the livers of the SD rats in control group, the experimental group, and the contrast group are shown respectively in FIG. 2 (A), (B) and (C).

Visceral Fat Weight

After the SD rats are sacrificed, visceral fat of each SD rat is obtained from the epididymis tissue and the perirenal adipose tissue, then washing, wiping and weighing the visceral fat. The visceral fat weights in the control group, the experimental group and the contrast group are respectively 29.8±1.92, 51.28±3.41, and 45.88±4.46 grams. It indicates the visceral fat weights in the experimental group and the contrast group are higher than that in the control group. Thus, with rotenone or not, the visceral fat weights of the SD rats fed with the high fat diet are increased.

Blood Biochemical Analysis

The blood biochemical analyses of cholesterol, triglyceride, and non-esterified fatty acids are examined. The liver function indexes of aspartate aminotransferase (AST) and alanine aminotransferase (ALT) are also analyzed. Table 1 below shows detailed data of the blood biochemical analyses and the liver function indexes.

TABLE 1

The data of blood biochemical analysis and liver function index in each group

| | Control group | Experimental group | Contrast group |
|---|---|---|---|
| Cholesterol (mg/dl) | 59.6 ± 3.03 | 73.4 ± 7.61 | 72.8 ± 4.31 |
| Triglyceride (mg/dl) | 45.1 ± 3.89 | 60.1 ± 10.15 | 55.5 ± 5.89 |
| Non-esterified fatty acids (μmol/L) | 0.43 ± 0.04 | 0.67 ± 0.06 | 0.58 ± 0.05 |
| AST (IU/L) | 63.1 ± 3.63 | 90.1 ± 13.68 | 72.4 ± 3.78 |
| ALT (IU/L) | 26.8 ± 3.24 | 39.4 ± 2.61 | 38.4 ± 3.80 |

The results show that the contents of the blood lipids, AST and ALT of the SD rats in the experimental group and the contrast group are higher than those in the control group. Additionally, the blood lipids and the liver function indexes of the SD rats treated with rotenone (the experiment group) are higher than those of the SD rats without treating with rotenone (the contrast group).

Liver Biochemical Analysis

The lipid extracts are obtained from the livers of the SD rats in each group to analyze the contents of total cholesterol, triglyceride, and non-esterified fatty acids, as shown below Table 2.

TABLE 2

The data of liver biochemical analysis in each group

| | Control group | Experimental group | Contrast group |
|---|---|---|---|
| Total cholesterol (mg/dl) | 87.38 ± 3.34 | 131.74 ± 5.30 | 109.57 ± 7.11 |
| Triglyceride (mg/dl) | 2.47 ± 0.19 | 6.78 ± 0.55 | 4.34 ± 0.64 |
| Non-esterified fatty acids (μmol/g) | 2.11 ± 0.27 | 5.02 ± 0.38 | 4.18 ± 0.36 |

The results show the contents of the liver lipids including the total cholesterol, triglyceride, and non-esterified fatty acids in the experimental group and the contrast group are higher than those in the control group. It indicates that, with rotenone or not, the contents of the liver lipids in the rats fed with the high calorie diet are increased.

Additionally, if oxidative stress, such as reactive oxygen species (ROS), is increased in vivo, lipid peroxides may be increased. Because the half life of the ROS is shorter than that of the lipid peroxides, the lipid peroxides, such as thiobarbituric acid-reactive-substance (TBARS), are used as the oxidative stress index. The livers of the SD rats in each group are respectively prepared to obtain homogeneous liquids for analyzing the concentration of the TBARS by a fluorophotometer. The results show the concentration of the TBARS in the experimental group is highest. The concentrations of the TBARS in the control group, the experimental group and the contrast group are respectively 0.51±0.05, 2.18±0.19 and 1.15±0.09 μM/mg protein. That means in the experimental group, the oxidative stress in the livers of the SD rats is highest.

In the NAFLD progression, when high oxidative stress is existed in a liver for a long time, inflammatory cytokines, such as tumor necrosis factor-alpha (TNF-α), are increased. After the SD rats are sacrificed, the concentration of the TNF-α is determined to analyze whether the inflammatory response is induced or not. The results show that the concentration of the TNF-α in the experimental group is higher than that in the contrast group, and the concentrations of the TNF-α in the experimental group and the contrast group are also higher than that in the control group. The concentrations of TNF-α in the control group, the experimental group, and the contrast group are respectively 13.96±1.05, 21.34±0.77, and 19.51±1.11 pg/mg protein. Following the results as set forth, the livers of rats in the experimental group have the inflammatory response. Additionally, the liver injury does not be induced during simple steatosis. But, once livers are existed in high oxidative stress, the liver injuries thereof from simple steatosis to necrosis or fibrosis are performed. Therefore, the collagen index (i.e. the fibrosis index), hydroxyproline, in the livers should be determined. The concentrations of the hydroxyproline in the control group, the experimental group, and the contrast group are 3.32±1.05, 6.68±0.77, and 4.05±1.11 μg/mg protein, respectively. It indicates the concentration of the hydroxyproline in the experimental group is higher than those of in the control group and the contrast group.

Mitochondrial Respiratory Transport Chain Enzymatic Complex Activities in Hepatocytes Rotenone is hydrophobic, and can diffuse to organelles including mitochondria. The rotenone has high affinity with mitochondrial respiratory transport chain complex I to inhibit the mitochondrial complex I activity, thereby resulting in electron leak, increase of ROS generation, and ATP synthesis impairment. Therefore, nicotinamide adenine dinucleotide (NADH) cytochrome c reductase (NCCR), succinate cytochrome c reductase (SCCR), and cytochrome c oxidase (CCO) are examined. The NCCR activity, the SCCR activity and the CCO activity respectively represent the mitochondrial complex I and III activity, the mitochondrial complex II and III activity, and the mitochondrial complex IV activity. The results show below Table 3.

TABLE 3

NCCR activity, SCCR activity and CCO activity in each group

| | Control group | Experimental group | Contrast group |
|---|---|---|---|
| NCCR (nmol/cytochrome c reduced/min/mg protein) | 2.68 ± 1.56 | 0.68 ± 0.26 | 2.32 ± 0.41 |
| SCCR (nmol/cytochrome c reduced/min/mg protein) | 0.17 ± 0.06 | 0.51 ± 0.05 | 0.42 ± 0.02 |
| CCO (nmol/cytochrome c oxidized/min/mg protein) | 6.53 ± 2.20 | 5.57 ± 2.88 | 4.04 ± 1.51 |

Combining with the results of the NCCR activity and the SCCR activity, mitochondrial complex I activity in the experimental group is lower than those in the control group and the contrast group. It indicates that if the rotenone is injected in the rats via the intraperitoneal injection, the rotenone diffuses into the hepatocytes into inhibit the mitochondrial complex I activity.

In summary, the rotenone, whose dosage is 2.5 mg/kg/day, is injected into the rats via the intraperitoneal injection, and meanwhile, the rats are fed with the 60% high fat diet. The results show that the mitochondrial respiratory transfer chain complex I activity is decreased in the rats treated with the rotenone, and the cell morphology thereof shows lipid drops and ballooning degeneration. The concentrations of the hydroxyproline, TBARS, TNF-α, blood lipids, and liver lipids are all increased. Thus, mitochondrial activity is decreased via injecting the mitochondrial inhibitor to cause mitochondrial dysfunction and increase oxidative stress so as to result in inflammation, thereby establishing an animal model of the nonalcoholic steatohepatitis (NASH).

The present invention has been described with some preferred embodiments thereof and it is understood that many changes and modifications in the described embodiments can be carried out without departing from the scope and the spirit of the invention that is intended to be limited only by the appended claims.

What is claimed is:

1. A method to induce fatty liver in an animal, comprising following steps:
   feeding an animal with a high calorie diet; and
   injecting a mitochondrial inhibitor into the animal to inhibit mitochondrial activity and to cause fat accumulation and inflammation in a liver of the animal.

2. The method to induce fatty liver in the animal as claimed in claim 1, wherein the mitochondrial inhibitor is injected into the animal by an intraperitoneal injection, an intramuscular injection, or an intravenous injection.

3. The method to induce fatty liver in the animal as claimed in claim 1, wherein the animal comprises a rodent.

4. The method to induce fatty liver in the animal as claimed in claim 3, wherein the rodent comprises a rat or a mouse.

5. The method to induce fatty liver in the animal as claimed in claim 4, wherein a species of the rat comprises Spraque-Daley, Spontaneously Hypertensive (SHR), Wistar, or Lewts.

6. The method to induce fatty liver in the animal as claimed in claim 4, wherein a species of the mouse comprises ICR, Balb/c, or C57BL6.

7. The method to induce fatty liver in the animal as claimed in claim 1, wherein the high calorie diet comprises a high fat diet, a high carbohydrate diet, a high fat and high carbohydrate diet, or a high cholesterol diet.

8. The method to induce fatty liver in the animal as claimed in claim 7, wherein fat calories of the high fat diet, carbohydrate calories of the high carbohydrate diet, or fat and carbohydrate calories of the high fat and high carbohydrate diet are in a range from 35% to 80% total calories.

9. The method to induce fatty liver in the animal as claimed in claim 7, wherein cholesterol in the high cholesterol diet is extra added therein, and an amount of the cholesterol is in a range from 0.1 to 2 wt % of the diet.

10. The method to induce fatty liver in the animal as claimed in claim 1, wherein the mitochondrial inhibitor comprises a mitochondrial complex I inhibitor, a mitochondrial complex III inhibitor, a mitochondrial complex IV inhibitor, or an adenosine triphosphate (ATP) synthase inhibitor.

11. The method to induce fatty liver in the animal as claimed in claim 10, wherein the mitochondrial complex I inhibitor comprises amytal, barbiturate, piericidin, or rotenone.

12. The method to induce fatty liver in the animal as claimed in claim 11, wherein a dosage of the rotenone injected into the animal is in a range from 0.1 to 4.0 mg/kg.

13. The method to induce fatty liver in the animal as claimed in claim 10, wherein the mitochondrial complex III inhibitor comprises antimycin A or dimercaprol.

14. The method to induce fatty liver in the animal as claimed in claim 10, wherein the mitochondrial complex IV inhibitor comprises cyanide, sulfide or azide.

15. The method to induce fatty liver in the animal as claimed in claim 10, wherein the ATP synthase inhibitor comprises oligomycin.

* * * * *